(12) United States Patent
Watanabe et al.

(10) Patent No.: US 11,091,730 B2
(45) Date of Patent: Aug. 17, 2021

(54) FILTER UNIT FOR FILTERING AND METHOD FOR COLLECTING CELLS IN A LIQUID CELL CULTURE MEDIUM

(71) Applicant: Murata Manufacturing Co., Ltd., Nagaokakyo (JP)

(72) Inventors: Junko Watanabe, Nagaokakyo (JP); Takashi Kondo, Nagaokakyo (JP); Masaru Banju, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 76 days.

(21) Appl. No.: 16/408,829

(22) Filed: May 10, 2019

(65) Prior Publication Data
US 2019/0276789 A1    Sep. 12, 2019

Related U.S. Application Data

(63) Continuation of application No. PCT/JP2017/038065, filed on Oct. 20, 2017.

(30) Foreign Application Priority Data

Nov. 18, 2016  (JP) .............................. JP2016-225227

(51) Int. Cl.
*C12M 1/12* (2006.01)
*C12M 1/00* (2006.01)
(Continued)

(52) U.S. Cl.
CPC .............. *C12M 29/04* (2013.01); *C12M 1/12* (2013.01); *C12M 3/06* (2013.01); *C12N 1/02* (2013.01); *C12N 5/00* (2013.01)

(58) Field of Classification Search
None
See application file for complete search history.

(56) References Cited

U.S. PATENT DOCUMENTS 2,193,006 A * 3/1940 Kufferath ................. D21F 1/46
162/357
2,641,365 A * 6/1953 Lundeen ................. B05B 15/00
210/153

(Continued)

FOREIGN PATENT DOCUMENTS

JP        H0889720 A      4/1996
JP       2004105139 A     4/2004
(Continued)

OTHER PUBLICATIONS

Machine translation of Description portion of WO2016140183 downloaded Sep. 27, 2020 (Year: 2020).*

(Continued)

*Primary Examiner* — Chester T Barry
(74) *Attorney, Agent, or Firm* — Arent Fox LLP

(57) ABSTRACT

A liquid cell culture medium collecting filter unit includes a porous metal membrane that filters out cells in a liquid cell culture medium, a support that holds a peripheral portion of the porous metal membrane. and a tubular member that has a hollow part serving a flow path for a liquid cell culture medium. The tubular member is connected to the support such that the flow path faces at least part of a main surface of the porous metal membrane.

10 Claims, 12 Drawing Sheets

(51) Int. Cl.
*C12N 5/00* (2006.01)
*C12N 1/02* (2006.01)
*C12M 3/06* (2006.01)

(56) References Cited

U.S. PATENT DOCUMENTS

| | | | | |
|---|---|---|---|---|
| 4,107,043 | A | * | 8/1978 | McKinney ............. B01D 35/02 |
| | | | | 210/232 |
| 2008/0093289 | A1 | * | 4/2008 | Zia ......................... B01D 27/07 |
| | | | | 210/436 |
| 2016/0041075 | A1 | | 2/2016 | Kamba et al. |
| 2016/0195458 | A1 | | 7/2016 | Kikuhara et al. |
| 2017/0203260 | A1 | | 7/2017 | Kondo et al. |

FOREIGN PATENT DOCUMENTS

| | | |
|---|---|---|
| WO | 2014192917 A1 | 12/2014 |
| WO | 2015019889 A1 | 2/2015 |
| WO | 2016140183 A1 | 9/2016 |
| WO | 2017022419 A1 | 2/2017 |

OTHER PUBLICATIONS

International Search Report issued for PCT/JP2017/038065, dated Jan. 23, 2018.
Written Opinion of the International Searching Authority issued for PCT/JP2017/038065, dated Jan. 23, 2018.

* cited by examiner

FIG. 11

| | Hole Size (μm) | Number of Spheroids | | Size of Spheroids (μm) | | | | Proportion of Remaining Cells (%) | Replacement Work Time |
|---|---|---|---|---|---|---|---|---|---|
| | | Before | After | Average Diameter (Ave.) | Standard Deviation (σ) | Maximum Diameter (Max) | Minimum Diameter (Min) | | |
| Porous Metal Membrane | 100 | 30 | 26 | 498.7 | 37.5 | 580 | 440 | 86.7 | 2ᵐ 46ˢ |
| | | | 19 | 689.3 | 43.5 | 830 | 610 | 63.3 | 2ᵐ 35ˢ |
| | 200 | 30 | 27 | 493.3 | 34.7 | 560 | 400 | 90.0 | 2ᵐ 45ˢ |
| | | | 29 | 711.0 | 55.3 | 780 | 630 | 96.7 | 2ᵐ 37ˢ |
| | 100 | 60 | 54 | 593.3 | 41.1 | 740 | 520 | 90.0 | 2ᵐ 52ˢ |
| | | | 53 | 627.8 | 45.6 | 810 | 560 | 88.3 | 2ᵐ 41ˢ |
| | 200 | 60 | 45 | 590.5 | 30.8 | 710 | 550 | 75.0 | 3ᵐ 00ˢ |
| | | | 58 | 656.8 | 55.4 | 900 | 580 | 96.7 | 2ᵐ 42ˢ |
| Centrifugation | | 30 | 16 | 492.0 | 36.0 | 470 | 400 | 53.3 | 22ᵐ 12ˢ |
| | | | 9 | 708.3 | 48.2 | 840 | 630 | 30.0 | 17ᵐ 53ˢ |
| | | 60 | 54 | 581.8 | 34.8 | 670 | 500 | 90.0 | 21ᵐ 44ˢ |
| | | | 56 | 644.2 | 35.6 | 750 | 580 | 96.3 | 17ᵐ 14ˢ |

FILTER UNIT FOR FILTERING AND METHOD FOR COLLECTING CELLS IN A LIQUID CELL CULTURE MEDIUM

CROSS REFERENCE TO RELATED APPLICATIONS

The present application is a continuation of International application No. PCT/JP2017/038065, filed Oct. 20, 2017, which claims priority to Japanese Patent Application No. 2016-225227, filed Nov. 18, 2016, the entire contents of each of which are incorporated herein by reference.

BACKGROUND OF THE INVENTION

The present invention relates to a liquid cell culture medium collecting filter unit, a liquid cell culture medium collecting method, and a liquid cell culture medium collecting kit.

Cell (cultured cell) growth requires a culture medium serving as a nutrient source. The culture medium needs to be replaced at regular intervals. A known method for replacing a culture medium uses, for example, centrifugation (see Japanese Unexamined Patent Application Publication No. 2004-105139, hereinafter Patent Document 1).

The method for replacing a culture medium using centrifugation is carried out, for example, as follows.

First, a cell-containing liquid cell culture medium in a container targeted for culture medium replacement is dispensed into centrifugation tubes. Next, each centrifugation tube is centrifuged, so that cells are concentrated at the bottom of each centrifugation tube. Next, the supernatant, which is part of the liquid cell culture medium, in each centrifugation tube is collected. Next, the cell-containing liquid cell culture medium that remains in each centrifugation tube is returned to the container. Next, a fresh liquid cell culture medium is placed in the container. Accordingly, replacement of the culture medium in the container is completed.

In the method for replacing culture media using centrifugation, the step of collecting the supernatant which is part of the liquid cell culture medium is performed by humans. Therefore, some workers may collect not only the supernatant but also cells and reduce the proportion of cells remaining in the container. In other words, there are large variations in the proportion of remaining cells depending on worker. In addition, it takes a long time to collect the liquid cell culture medium.

To solve the above-described issues, it is an object of the present invention is to provide a liquid cell culture medium collecting filter unit, a liquid cell culture medium collecting method, and a liquid cell culture medium collecting kit, which can reduce variations in the proportion of remaining cells and can shorten the time required to collect a liquid cell culture medium.

BRIEF SUMMARY OF THE INVENTION

A liquid cell culture medium collecting filter unit according to an aspect of the invention comprises a porous metal membrane that filters out cells in a liquid cell culture medium, a support that holds a peripheral portion of the porous metal membrane, and a tubular member that has a hollow part serving as a flow path for the liquid cell culture medium. The tubular member is connected to the support such that the flow path faces at least part of a main surface of the porous metal membrane.

The support preferably includes first and second frame members between which the peripheral portion of the porous metal membrane is sandwiched. The peripheral portion of the porous metal membrane preferably has a surface located between first and second spaced bent portions that is sandwiched between the first and second frame members. The surface preferably has at least one stripe-shaped protrusion located between on the surface. More preferably, the surface has a plurality of the stripe-shaped protrusions located between the first and second bent portions and the stripe-shaped protrusions are oriented in random directions.

The porous metal membrane is preferably flush or substantially flush with an opening plane defined by an end portion of the protrusion of the holding member. As used herein, the term "substantially flush" means that the gap between S2 and element 2 of FIG. 4 (as measured in the vertical direction is FIG. 4) is 400 μm or less.

As annular protrusion that protrudes in a thickness direction of the support is preferably provided on a main surface of the support and extends away from the tubular member. In such a case, the porous metal membrane is preferably disposed on an inner side of the annular protrusion.

A liquid cell culture medium collecting method according to an aspect of the present invention includes the following acts:

placing a liquid cell culture medium collecting filter unit in a container that contains a cell-containing liquid cell culture medium, the liquid culture medium collecting filter unit including a porous metal membrane that filters out cells in the liquid cell culture medium, a support that holds a peripheral portion of the porous metal membrane, and a tubular member that has a hollow part serving as a flow path for the liquid cell culture medium and is connected to the support such that the flow path faces at least part of a main surface of the porous metal membrane; and passing the liquid cell culture medium in the container through the flow path and the porous metal membrane and collecting the liquid cell culture medium outside the container.

The liquid cell culture medium collecting method preferably further includes supplying a fresh liquid cell culture medium to the container after at least some of the liquid cell culture medium has been collected outside the container. It is useful to pass the liquid cell culture medium located in the container passes through the porous metal membrane in a first direction as it is being moved from the container to a location outside the container and to pass the fresh liquid cell culture medium through the porous metal membrane in a second direction, opposite to the first direction, as it is supplied to the container.

After the fresh liquid cell culture medium has been supplied to the container supplying, it is preferable to cause at least some of the liquid cell culture medium located in the container to flow through the flow path and the porous metal membrane and to collect the liquid cell culture medium outside the container.

A liquid cell culture medium collecting kit according to another aspect of the invention comprising the liquid cell culture medium collecting filter unit described above.

The liquid cell culture medium collecting filter unit and the liquid cell culture medium collecting method according to the aspects of the present invention can reduce variations in the proportion of remaining cells and can shorten the time required to collect a liquid cell culture medium.

BRIEF DESCRIPTION OF THE DRAWINGS

FIG. 11 is a table showing the proportion of remaining cells and the replacement time when the liquid cell culture medium in the container is replaced by using the liquid cell culture medium collecting filter unit in FIG. 1, where the table also shows the proportion of remaining cells and the replacement time when the liquid cell culture medium in the container is replaced by using a centrifuge in the Comparative Example.

DESCRIPTION OF THE PREFERRED EMBODIMENTS

Figure 1:
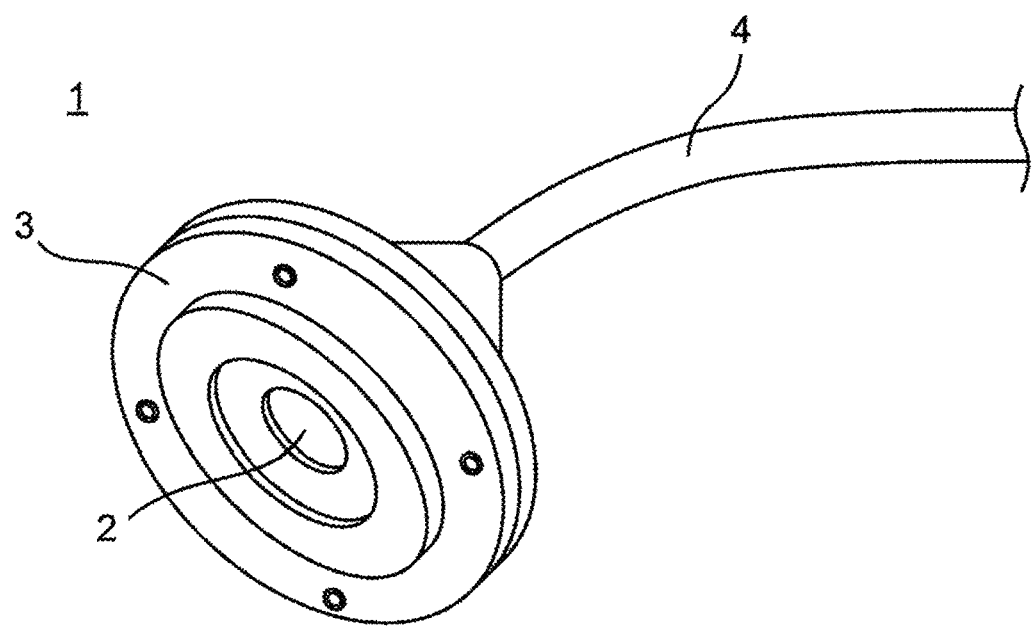
FIG. 1 is a perspective view illustrating the schematic structure of a liquid cell culture medium collecting filter unit according to an embodiment of the present invention.

A liquid cell culture medium collecting filter unit according to an aspect of the invention comprises a porous metal membrane that filters out cells in a liquid cell culture medium, a support that holds a peripheral portion of the porous metal membrane, and a tubular member that has a hollow part serving as a flow path for the liquid cell culture medium. The tubular member is connected to the support such that the flow path faces at least part of a main surface of the porous metal membrane.

Since this structure includes the porous metal membrane that filters out cells in the liquid cell culture medium, the cells can remain in the container as a result of filtering out the cells by using the porous metal membrane, and only the liquid cell culture medium can be collected through liquid culture medium flow paths. This can reduce variations in the proportion of remaining cells and achieve a high proportion of remaining cells. Since cells are less likely to be attached to a porous metal membrane than to, for example, a porous resin membrane, it is possible to prevent inhibition of collection of the liquid cell culture medium caused by clogging of membrane holes with cells. Thus, the time required to collect the liquid cell culture medium can be shortened.

The holding member preferably includes a first frame member and a second frame member between which the peripheral portion of the porous metal membrane is sandwiched. The peripheral portion of the porous metal membrane preferably has a first bent portion and a second bent portion. The peripheral portion of the porous metal membrane is preferably sandwiched between the first frame member and the second frame member so as to have a stripe-shaped protrusion between the first bent portion and the second bent portion. According to this structure, the stripe-shaped protrusion between the first bent portion and the second bent portion in the porous metal membrane can increase the friction between the peripheral portion of the porous metal membrane and the first frame member and the second frame member. This structure can avoid the porous metal membrane from falling out of the frame members even if the liquid cell culture medium is collected at a high flow rate. The liquid cell culture medium can thus be collected in a short time.

A plurality of the stripe-shaped protrusions is preferably provided between the first bent portion and the second bent portion, and the stripe-shaped protrusions are preferably oriented in random directions. This structure can increase the friction between the peripheral portion of the porous metal membrane and the first frame member and the second frame member and can further improve the holding power of the first frame member and the second frame member used to hold the porous metal membrane.

An annular protrusion that protrudes in the thickness direction of the holding member is preferably provided on a main surface of the holding member away from the tubular member. The porous metal membrane is preferably disposed on the inner side of the protrusion. According to this structure, the porous metal membrane can be positioned closer to the bottom of the container, and the liquid surface can be lowered to the main surface below the porous metal membrane. The amount of the collected liquid cell culture medium can thus be increased without reducing the proportion of remaining cells. Since the porous metal membrane positioned closer to the bottom of the container contacts a large amount of the liquid cell culture medium, the cells attached to the porous metal membrane are washed away, which can make it difficult to cause clogging. When a liquid cell culture medium is supplied through the porous metal membrane after collection of the liquid cell culture medium, the cells attached to the porous metal membrane tend to be detached from the porous metal membrane during the passage of the liquid cell culture medium. This can further avoid clogging. As a result, the working time can be shortened. This configuration can also suppress an increase in pressure in the tubular member caused by clogging and can reduce the stress on the cells.

The porous metal membrane is preferably flush or substantially flush with an opening plane defined by the end portion of the protrusion of the holding member. This structure enables the porous metal membrane to be positioned still closer to the bottom of the container and can increase the amount of the collected liquid cell culture medium without reducing the proportion of remaining cells. This structure can also prevent the porous metal membrane from being clogged with cells to shorten the working time and can reduce the stress on the cells.

A liquid cell culture medium collecting method according to an aspect of the present invention includes a filter unit-placing step of placing, in a container that contains a cell-containing liquid cell culture medium, a liquid cell culture medium collecting filter unit including a porous metal membrane that filters out cells in the liquid cell culture medium, a holding member that holds the peripheral portion of the porous metal membrane, and a tubular member that has a hollow part serving as a flow path for the liquid cell culture medium and is connected to the holding member such that the hollow part faces at least part of a main surface of the porous metal membrane; and a collecting step of introducing the liquid cell culture medium in the container to the flow path through the porous metal membrane and collecting the liquid cell culture medium outside the container.

Since the liquid cell culture medium in the container is sucked through the porous metal membrane in this method, the cells can remain in the container as a result of filtering out the cells by using the porous metal membrane, and only the liquid cell culture medium can be collected through the liquid culture medium flow paths. This configuration can reduce variations in the proportion of remaining cells. Since cells are less likely to be attached to a porous metal membrane than to, for example, a porous resin membrane, it is possible to prevent inhibition of collection of a liquid cell culture medium caused by clogging of membrane holes with cells. Thus, the time required to collect the liquid cell culture medium can be shortened.

The method may further include, after the collecting step, a supplying step of supplying a fresh liquid cell culture medium to the container. According to this method, the liquid cell culture medium in the container can be replaced by a fresh liquid cell culture medium.

In the supplying step, the fresh liquid cell culture medium may flow through the flow path and may be supplied to the container through the porous metal membrane. According to this method, even if cells are attached to the porous metal membrane, the cells can be detached from the porous metal membrane (that is, the porous metal membrane can be backwashed) under the pressure of the fresh liquid cell culture medium. As a result, the time required to replace the liquid cell culture medium can be shortened.

The method may further include, after the supplying step, a re-collecting step of introducing the liquid cell culture medium in the container to the flow path through the porous metal membrane and collecting the liquid cell culture medium outside the container. According to this method, the liquid cell culture medium can be continuously collected by using the same porous metal membrane.

A liquid cell culture medium collecting kit according to an aspect of the present invention is a liquid cell culture medium collecting kit used in the liquid cell culture medium collecting method and includes the liquid cell culture medium collecting filter unit. This structure can reduce variations in the proportion of remaining cells and can shorten the time required to collect the liquid cell culture medium.

Referring ow to the drawings wherein like numerals indicate like elements, FIGS. 1 to 5 illustrate the structure of a liquid cell culture medium collecting filter unit according to a preferred embodiment of the present invention.

Figure 2:
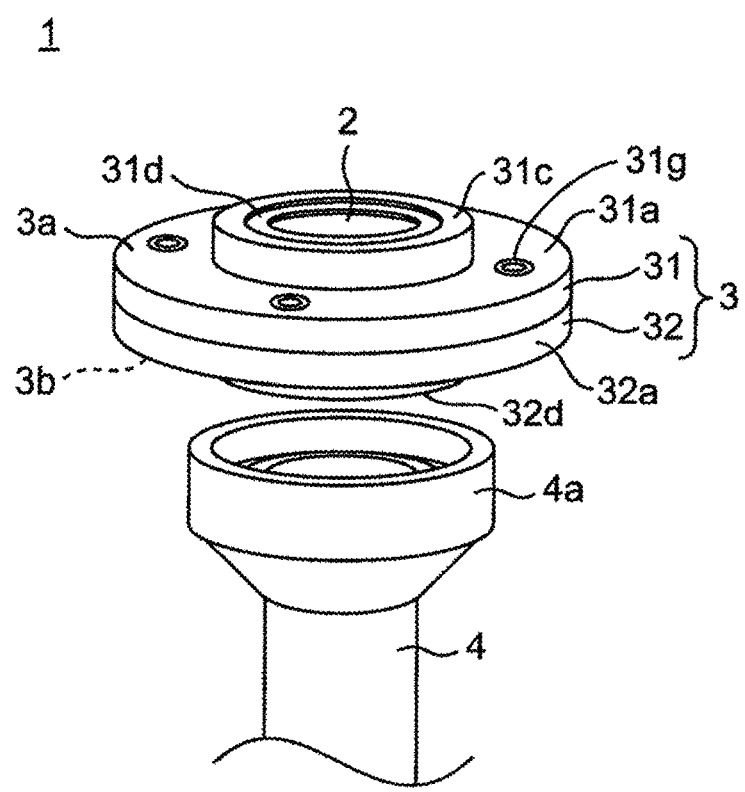
FIG. 2 is an exploded perspective view of the liquid cell culture medium collecting filter unit in FIG. 1.
Figure 3:
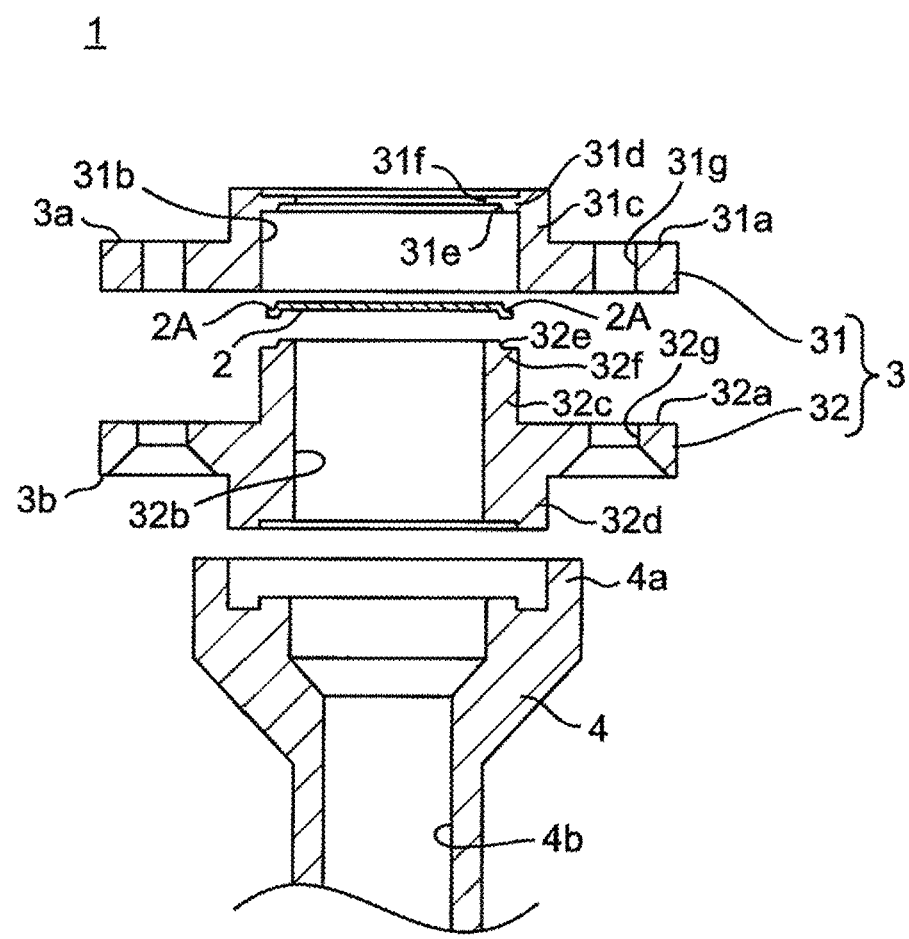
FIG. 3 is an exploded sectional view of the liquid cell culture medium collecting filter unit in FIG. 1.
Figure 4:
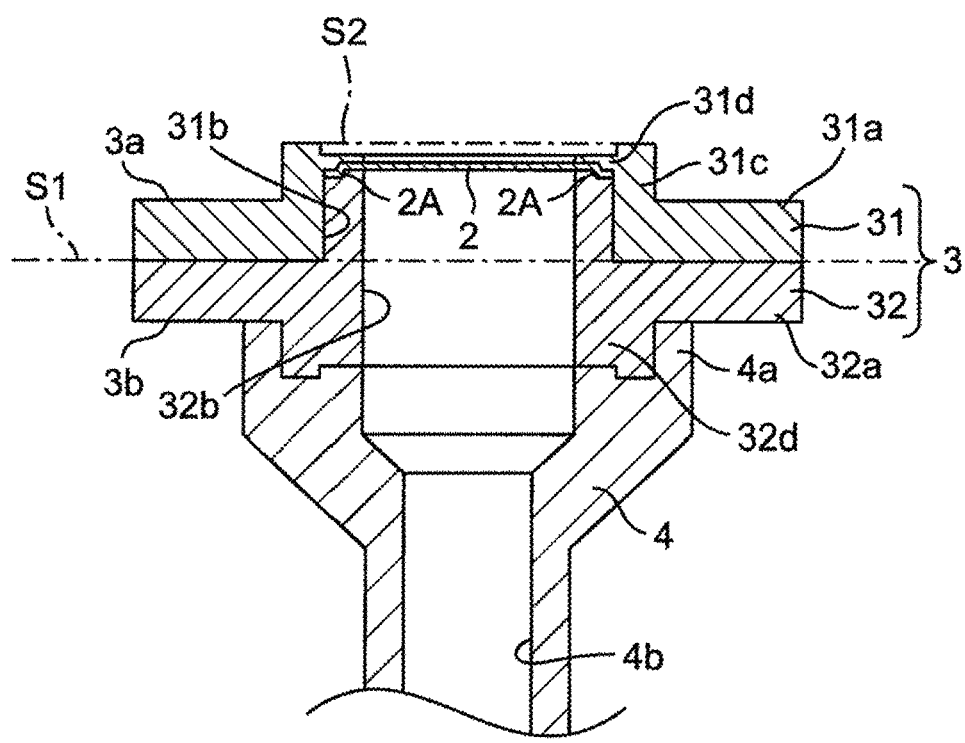
FIG. 4 is an assembly sectional view of the liquid cell culture medium collecting filter unit in FIG. 1.
Figure 5:
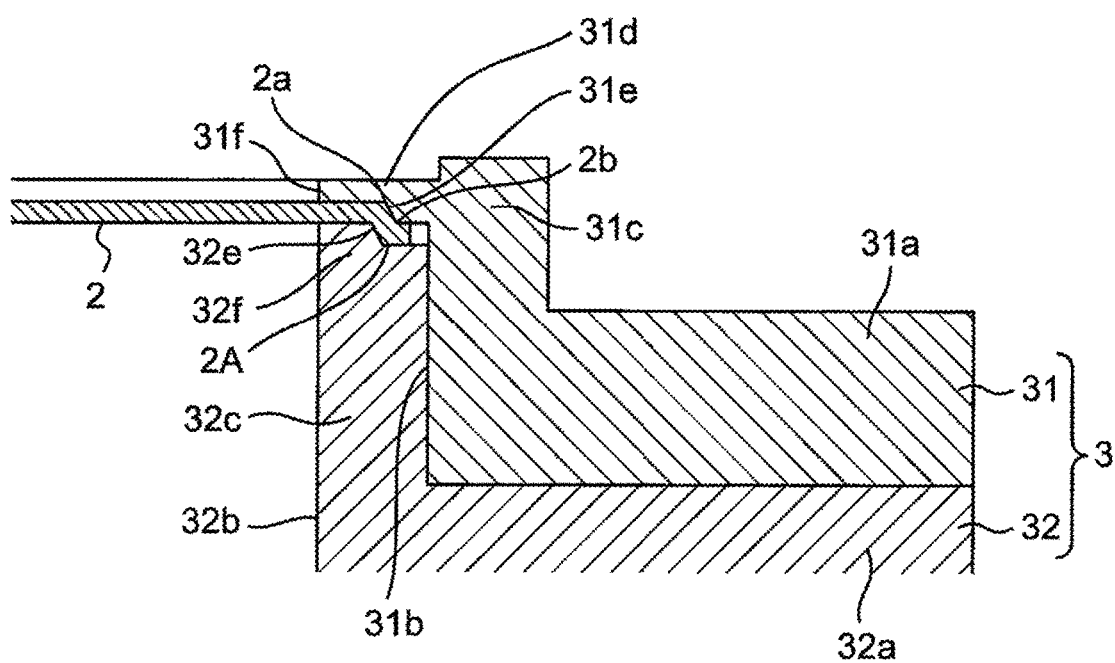
FIG. 5 is a partially enlarged sectional view of FIG. 4.

As illustrated in FIG. 1 and FIG. 2, a liquid cell culture medium collecting filter unit 1 includes a porous metal membrane 2, a holding member 3, and a tubular member 4, which is connected to the holding member 3. The holding member 3 holds a peripheral portion 2A of the porous metal membrane 2 as illustrated in FIGS. 3 to 5. In the preferred embodiment, the holding member 3 includes first and second frame members 31 and 32.

As best shown in FIGS. 4 and 5, the peripheral portion 2A of the porous metal membrane 2 can be sandwiched between the first and second frame members 31 and 32. The first frame member 31 includes an annular flat portion 31a and an annular protrusion 31c, which is positioned at the section around a central through-hole 31b so as to protrude away from the tubular member 4. The flat portion 31a has a diameter of, for example, 18 mm. The flat portion 31a has a thickness of, for example, 1.5 mm. The protrusion 31c has a height of, for example, 1.5 mm.

An annular flange 31d, which protrudes toward the center of the through-hole 31b, is formed on the inner surface of the annular protrusion 31c. The flange 31d is provided at a distance of, for example, 0.1 mm from the top of the protrusion 31c toward the flat portion 31a. As best shown in FIG. 3, an end portion 31f of the flange 31d close to the center of the through-hole 31b has a reduced thickness so as to form a slope surface 31e on the tubular member 4 side. The thickness of the flange 31d adjacent to the protrusion 31c is, for example, 0.3 mm. The thickness of the end portion 31f of the flange 31d is, for example, 0.2 mm. The angle of the slope surface 31e is, for example, 45 degrees.

As best shown in FIG. 3, the second frame member 32 includes an annular flat portion 32a, an annular protrusion 32c (which is positioned at the section around a central through-hole 32b so as to protrude away from the tubular member 4), and an annular protrusion 32d (which is positioned at the section around the central through-hole 32b so as to protrude toward the tubular member 4). The flat portion 32a has a diameter of, for example, 18 mm. The flat portion 32a has a thickness of, for example, 1.5 mm. The protrusion 32d has a height of, for example, 1.5 mm.

The protrusion 32c has an outer diameter that is slightly smaller than the diameter of the through-hole 31b such that the protrusion 32c can be inserted into the through-hole 31b of the first frame member 31. An end portion 32f of the protrusion 32c is shaped in conformance with the shape of the flange 31d on the tubular member 4 side. In other words, the end portion 32f has a slope surface 32e corresponding to the slope surface 31e.

As illustrated in FIG. 4, the porous metal membrane 2 is held so as to have tension in the plane direction when the peripheral portion 2A is sandwiched between the flange 31d of the first frame member 31 and the end portion 32f of the protrusion 32c of the second frame member 32 and lies along the slope surface 31e and the slope surface 32e. The peripheral portion 2A of the porous metal membrane 2 is sandwiched at the position spaced from a central plane S1 (which is a central plane in the thickness direction of the holding member 3) in the thickness direction. In the preferred embodiment, the porous metal membrane 2 is disposed on the inner side of the annular protrusion 31c and is substantially flush with an opening plane S2 defined by the end portion of the annular protrusion 31c.

As illustrated in FIG. 3, the flat portion 31a of the first frame member 31 has a plurality of through-holes 31g, which penetrates the first frame member 31 in the thickness direction. The through-holes 31g are arranged at regular intervals in the circumferential direction of the flat portion 31a. Similarly, the flat portion 32a of the second frame member 32 has a plurality of through-holes 32g, which penetrates the second frame member 32 in the thickness direction. The through-holes 32g are arranged at regular intervals in the circumferential direction of the flat portion 32a so as to correspond to the through-holes 31g. The first frame member 31 and the second frame member 32 are fixed to each other by inserting fastening members (not illustrated), such as screws, into the respective through-holes 31g and 32g while the protrusion 32c of the second frame member 32 is inserted in the through-hole 31b of the first frame member 31.

The tubular member 4 includes a fitting portion 4a, which can be fitted to the protrusion 32d of the second frame member 32. The tubular member 4 is detachably attached to the second frame member 32 by fitting the fitting portion 4a onto the outer surface of the protrusion 32d of the second frame member 32. The tubular member 4 has a hollow part 4b serving as a flow path for the liquid cell culture medium. The tubular member 4 is connected to the second frame member 32 such that the hollow part 4b faces at least part of the main surface of the porous metal membrane 2. With this configuration, the liquid cell culture medium that has passed through the porous metal membrane 2 can be collected through the hollow part 4b which defines a flow path for the liquid cell culture medium.

Examples of the materials of the first frame member 31, the second frame member 32, and the tubular member 4 include metals, such as duralumin, aluminum, and stainless steel (SUS); and resins, such as polyethylene, polystyrene, polypropylene, polycarbonate, polyacetal, and polyetherimide.

Figure 6:
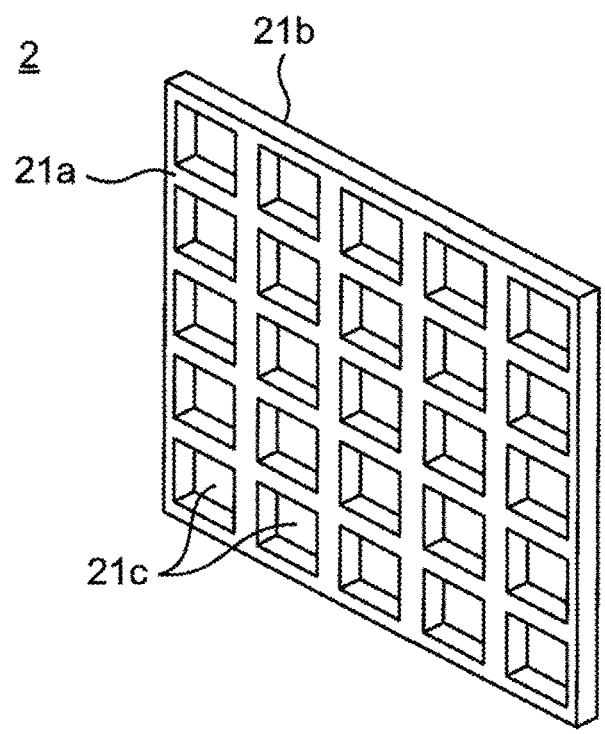
FIG. 6 is a partially enlarged perspective view illustrating the schematic structure of a porous metal membrane.

FIG. 6 is a partially enlarged perspective view schematically illustrating the structure of an exemplary porous metal membrane 2 used to filter out cells contained in the liquid cell culture medium. The porous metal membrane 2 is used to filter out cells (e.g., spheroids) contained in the liquid cell culture medium.

As illustrated in FIG. 6, the porous metal membrane 2 has a pair of opposing main surfaces 21a and 21b and a plurality of through-holes 21c which penetrates both the main surfaces 21a and 21b. The through-holes 21c separate cells from the liquid cell culture medium. The shape and size of the through-holes 21c are appropriately set according to the shape and size of the cells. The through-holes 21c may be arranged, for example, at regular intervals or periodically. The shape of the through-holes 21c is, for example, square as viewed from the main surface 21a side of the porous metal membrane 2. In the illustrated embodiment, the through-holes 21c are arranged in a square lattice. The size of each through-hole 21c is, for example, 0.1 µm or more and 600 µm or less in length and 0.1 µm or more and 600 µm or less in width. The interval between the through-holes 21c is, for example, larger than the size of the through-holes 21c by a factor of preferably 1 time or more and 10 times or less, and more preferably 3 times or less. The opening ratio of the through-holes 21c in the porous metal membrane 2 is, for example, 10% or more. The through holes 21c can take other shapes and may be, for example, regular hexagons as viewed from the main surface 21a side of the porous metal membrane 2. The through-holes 21c may be arranged to form a honeycomb structure.

Examples of the material of the porous metal membrane 2 include gold, silver, copper, platinum, nickel, stainless steel, palladium, titanium, cobalt, alloys thereof, and oxides thereof. The size of the porous metal membrane 2 is, for example, 6 mm in diameter. The thickness of the porous metal membrane 2 is, for example, 0.1 µm or more and 100 µm or less and preferably 0.1 µm or more and 50 µm or less. The porous metal membrane 2 has, for example, a circular, elliptical, or polygonal contour. In the preferred embodiment, the porous metal membrane 2 has a circular outer periphery. The peripheral portion of the porous metal membrane 2 may have the through-holes 21c or may not have the through-holes 21c.

Figure 8:
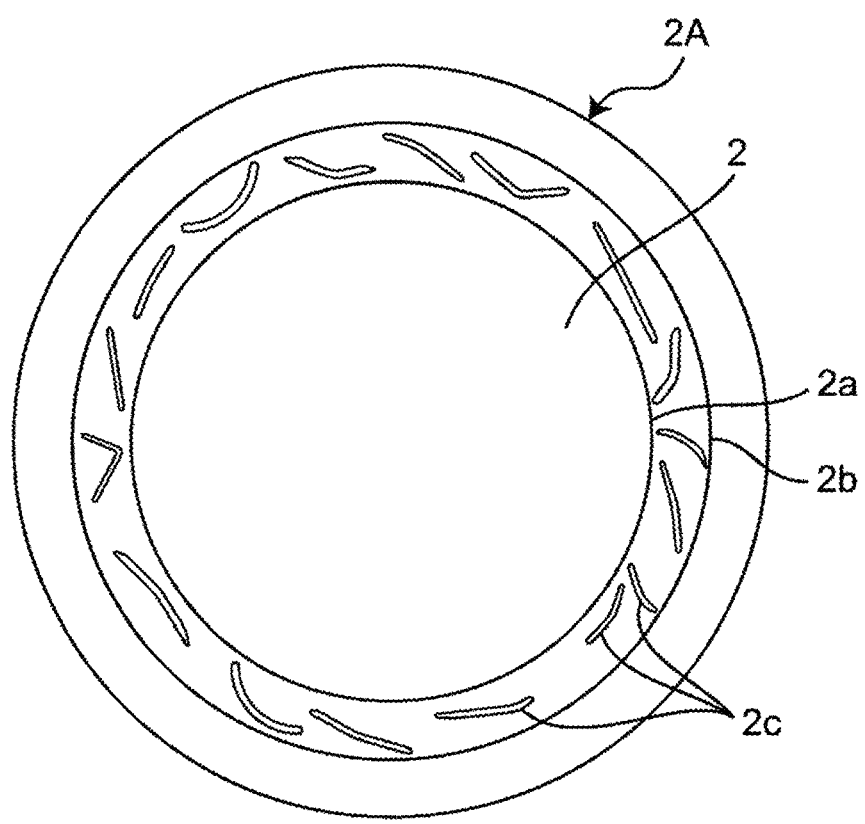
FIG. 8 is a plane view illustrating the schematic structure of the porous metal membrane.

In the embodiment illustrated in FIG. 5, the peripheral portion 2A of the porous metal membrane 2 is sandwiched between the slope surface 31e of the first frame member 31 and the slope surface 32e of the second frame member 32 so as to have a first bent portion 2a and a second bent portion 2b. As illustrated in FIG. 8, the peripheral portion 2A of the porous metal membrane 2 is sandwiched so as to have stripe-shaped protrusions 2c between the first bent portion 2a and the second bent portion 2b. The stripe-shaped protrusions 2c refer to parts that protrude from one of the main surfaces of the porous metal membrane 2 and have a height that is 0.1 times or more and 2 times or less the thickness of the porous metal membrane 2. The stripe-shaped protrusions 2c can increase the friction between the peripheral portion 2A of the porous metal membrane 2 and the first frame member 31 and the second frame member 32.

As illustrated in FIG. 8, a plurality of the stripe-shaped protrusions 2c is provided between the first bent portion 2a and the second bent portion 2b, and the stripe-shaped protrusions 2c are preferably oriented in random directions. This structure can increase the friction between the peripheral portion 2A of the porous metal membrane 2 and the first frame member 31 and the second frame member 32 and can further improve the holding power of the first frame member 31 and the second frame member 32 used to hold the porous metal membrane 2.

The stripe-shaped protrusions 2c may be formed of, for example, the wrinkles formed in the porous metal membrane 2. The term "wrinkles" refers to fine stripes created as a result of loosening or shrinking of the porous metal membrane 2. In this case, the porous metal membrane 2 itself can form the stripe-shaped protrusions 2c, and there is no need to separately dispose members serving as the stripe-shaped protrusions 2c.

Figure 9:
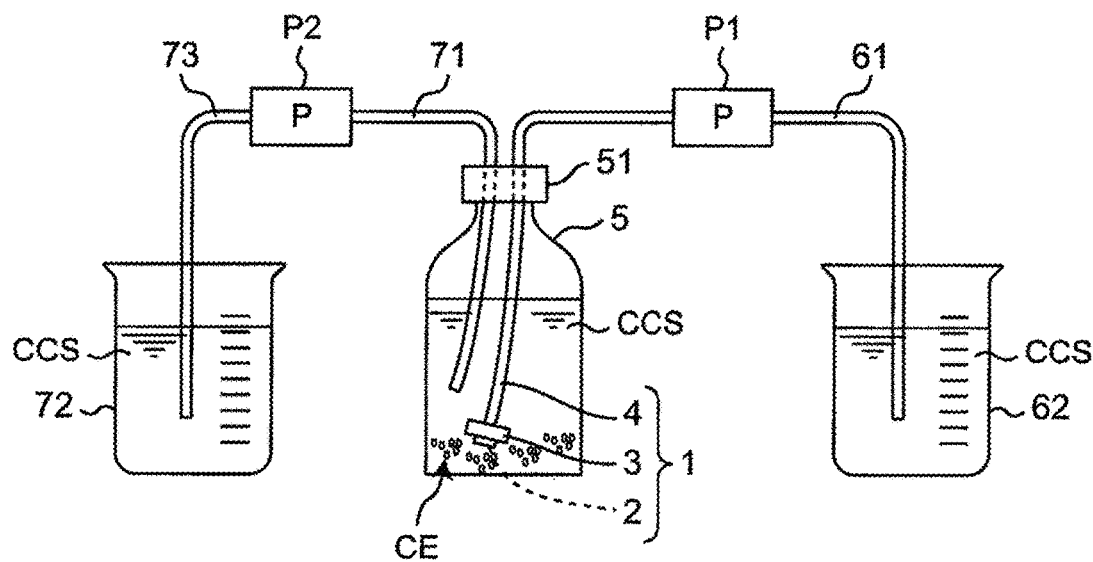
FIG. 9 is a schematic diagram illustrating an example of a liquid cell culture medium collecting and replacing method.

Next, a liquid cell culture medium collecting and replacing method using the liquid cell culture medium collecting filter unit 1 according to the preferred embodiment will be described. FIG. 9 is a schematic diagram illustrating an example of the liquid cell culture medium collecting and replacing method.

First, as illustrated in FIG. 9, the liquid cell culture medium collecting filter unit 1 is placed in a container 5 that contains a liquid cell culture medium CCS containing cells CE. More specifically, one end portion of the tubular member 4 is placed in the container 5 such that the porous metal membrane 2 is positioned in the liquid cell culture medium CCS.

The other end portion of the tubular member 4 is connected to a pump P1. The pump P1 is connected to a collection pipe 61 through which the liquid cell culture medium CCS collected from the container 5 flows into a liquid culture medium collection container 62. To supply a fresh liquid cell culture medium CCS to the container 5, one end portion of a supply pipe 71 is placed in the container 5. The other end portion of the supply pipe 71 is connected to a pump P2. The pump P2 is connected to a suction pipe 73 through which the fresh liquid cell culture medium CCS is sucked from a liquid culture medium storage container 72. The container 5 has a bottle shape and has a cap 51, which closes the opening. The tubular member 4 and the supply pipe 71 penetrate the cap 51.

Next, the pump P1 is driven to suck the liquid cell culture medium CCS in the container 5 through the porous metal membrane 2, and the liquid cell culture medium CCS is collected in the liquid culture medium collection container 62, which is located outside the container 5, through the tubular member 4. Since the porous metal membrane 2 filters out (e.g., retains) the cells CE in the container 5 at this time, the cells CE remain in the container 5, and only the liquid cell culture medium CCS is collected in the liquid culture medium collection container 62 through the tubular member 4 and the collection pipe 61.

Next, the pump P2 is driven to supply the fresh liquid cell culture medium CCS in the liquid culture medium storage container 72 to the container 5 through the suction pipe 73 and the supply pipe 71 (supplying step). Accordingly, a fresh culture medium can be prepared by replacing the liquid cell culture medium CCS in the container 5.

Next, after a predetermined period of time has elapsed, the pump P1 is driven to suck the liquid cell culture medium CCS in the container 5 through the porous metal membrane 2, and the liquid cell culture medium CCS is collected in the liquid culture medium collection container 62, which is located outside the container 5, through the tubular member 4.

Next, the pump P2 is driven to supply the fresh liquid cell culture medium CCS in the liquid culture medium storage container 72 to the container 5 through the suction pipe 73 and the supply pipe 71. Accordingly, the fresh culture medium can be prepared by replacing the liquid cell culture medium CCS in the container 5 again.

Since the liquid cell culture medium collecting filter unit 1 includes the porous metal membrane 2 according to the preferred embodiment, the cells CE can remain in the container 5 as a result of filtering out the cells CE by using the porous metal membrane 2, and only the liquid cell culture medium CCS can be collected through the liquid culture medium flow paths (the tubular member 4 and the collection pipe 61). This configuration can reduce variations in the proportion of cells CE remaining in the container 5.

In the preferred embodiment, since the cells CE are less likely to be attached to the porous metal membrane 2 than to, for example, a porous resin membrane, it is possible to prevent inhibition of collection of the liquid cell culture medium CCS caused by clogging of membrane holes with the cells CE. Thus, the time required to collect the liquid cell culture medium CCS can be shortened.

Since the porous metal membrane 2 has higher mechanical stiffness than, for example, a porous resin membrane or the like, the porous metal membrane 2 is unlikely to change in size even when always immersed in the liquid cell culture medium CCS or even under high pressure. Therefore, the collection and replacement of the liquid cell culture medium can be automated and repeated by controlling the drive of the pumps P1 and P2.

According to the preferred embodiment, there is no need to remove the cap 51 from the container 5 at the time of the collection and replacement of the liquid cell culture medium. This makes it possible to obtain a substantially sealed space in the container 5 so as to prevent contamination by bacteria and the like.

According to the preferred embodiment, the holding member 3 includes the first frame member 31 and the second frame member 32 between which the peripheral portion 2A of the porous metal membrane 2 is sandwiched. The peripheral portion 2A of the porous metal membrane 2 has the first bent portion 2a and the second bent portion 2b. The peripheral portion 2A of the porous metal membrane 2 is sandwiched between the first frame member 31 and the second frame member 32 so as to have the stripe-shaped protrusions 2c between the first bent portion 2a and the second bent portion 2b. According to this structure, the stripe-shaped protrusions 2c between the first bent portion 2a and the second bent portion 2b in the porous metal membrane 2 can increase the friction between the peripheral portion 2A of the porous metal membrane 2 and the first frame member 31 and the second frame member 32. This structure can avoid the porous metal membrane 2 from falling out of the position between the first frame member 31 and the second frame member 32 even if the liquid cell culture medium CCS is collected at a high flow rate. The liquid cell culture medium CCS can thus be collected in a short time.

According to the preferred embodiment, a plurality of the stripe-shaped protrusions 2c is provided between the first bent portion 2a and the second bent portion 2b, and the stripe-shaped protrusions 2c are oriented in random directions. This structure can increase the friction between the peripheral portion 2A of the porous metal membrane 2 and the first frame member 31 and the second frame member 32 and can further improve the holding power of the first frame member 31 and the second frame member 32 used to hold the porous metal membrane 2.

According to the preferred embodiment, the annular protrusion 31c is provided on a main surface 3a of the holding member 3 and projects away from the tubular member 4. The porous metal membrane 2 is disposed on the inner side of the protrusion 31c. This structure enables the porous metal membrane 2 to be positioned closer to the bottom of the container 5 and can increase the amount of the collected liquid cell culture medium CCS without reducing the proportion of remaining cells CE. The liquid surface can be lowered to the main surface below the porous metal membrane 2. The amount of the collected liquid cell culture medium CCS can thus be increased without reducing the proportion of remaining cells CE. Since the porous metal membrane 2 positioned closer to the bottom of the container 5 contacts a large amount of the liquid cell culture medium, the cells attached to the porous metal membrane 2 are washed away, which can make it difficult to cause clogging. When a liquid cell culture medium CCS is supplied through the porous metal membrane 2 after collection of the liquid cell culture medium, the cells CE attached to the porous metal membrane 2 tend to be detached from the porous metal membrane 2 during the passage of the liquid cell culture medium CCS. This can further avoid clogging. As a result, the working time can be shortened. This configuration can also suppress an increase in pressure in the tubular member 4 caused by clogging and can reduce the stress on the cells.

According to the preferred embodiment, the porous metal membrane 2 is flush or substantially flush with an opening plane defined by the end portion 31f of the protrusion 31c of the holding member 3. The porous metal membrane 2 can be positioned still closer to the bottom of the container 5, and the amount of the collected liquid cell culture medium CCS can be increased without reducing the proportion of remaining cells CE. The porous metal membrane 2 can be prevented from being clogged with cells to shorten the working time and to reduce the stress on the cells.

According to the preferred embodiment, the collecting step is followed by the supplying step, and thus the liquid cell culture medium in the container 5 can thus be replaced by a fresh liquid cell culture medium.

According to the preferred embodiment, the supplying step is followed by the re-collecting step, and thus the liquid cell culture medium CCS can be continuously collected by using the same porous metal membrane 2.

The present invention is not limited to the above-described embodiment and can be carried out in various other aspects. For example, in the foregoing description, the fitting portion 4a of the tubular member 4 is fitted onto the protrusion 32d of the second frame member 32, whereby the tubular member 4 is attached to the second frame member 32. The present invention is not limited to this configuration. For example, one of the fitting portion 4a of the tubular member 4 and the protrusion 32d of the second frame member 32 may have an external thread, and the other may have an internal thread, such that the tubular member 4 and the second frame member 32 can be screwed to each other. Alternatively, for example, the second frame member 32 may have a locking claw (e.g., a hook-shaped claw), and the tubular member 4 may have a receptacle (e.g., a hole engageable with the hook-shaped claw), such that the locking claw can be fitted into the receptacle.

In the foregoing description, the pump P1 is driven to suck the liquid cell culture medium CCS in the container 5 through the porous metal membrane 2, and the liquid cell culture medium CCS is collected in the liquid culture medium collection container 62, which is located outside the container 5, through the tubular member 4. The present invention is not limited to this configuration. Alternatively, the liquid cell culture medium CCS in the container 5 may be introduced to the tubular member 4 through the porous metal membrane 2 and collected outside the container 5. For example, the liquid cell culture medium CCS in the container 5 is not sucked into the tubular member 4 but pressure-fed to the tubular member 4 through the porous metal membrane 2.

Figure 10:
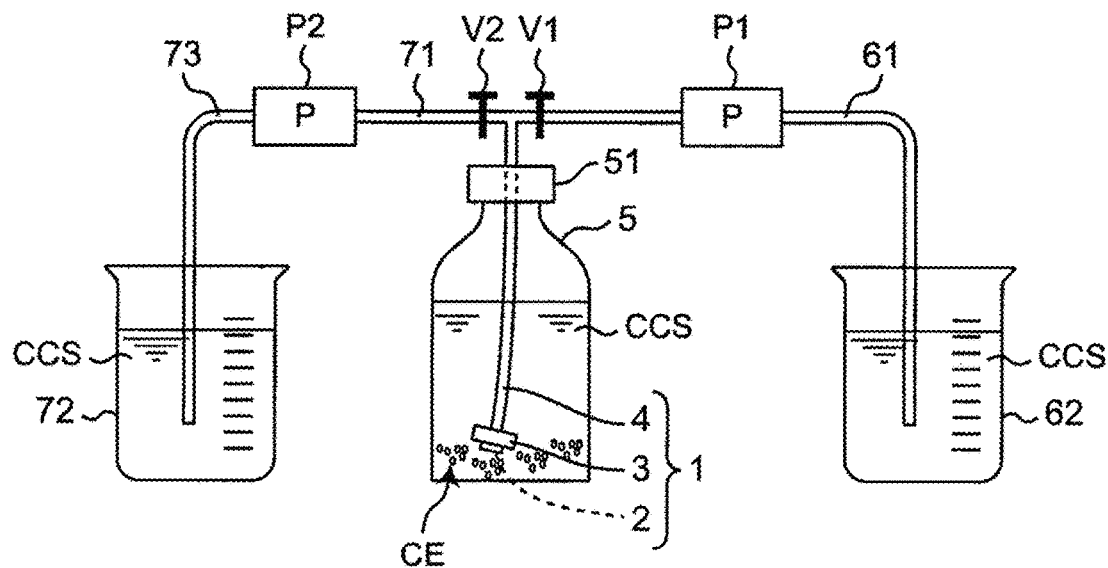
FIG. 10 is a schematic diagram illustrating a modification of the liquid cell culture medium collecting and replacing method.

In the foregoing description, the fresh liquid cell culture medium CCS in the liquid culture medium storage container 72 is supplied to the container 5 through the supply pipe 71 in the supplying step. The present invention is not limited to this configuration. For example, as illustrated in FIG. 10, the other end portion of the tubular member 4 may be branched, and the branches of the branched tubular member may be respectively connected to the pumps P1 and P2. According to this structure, the fresh liquid cell culture medium CCS in the liquid culture medium storage container 72 can flow through the tubular member 4 and can be supplied to the container 5 through the porous metal membrane 2. As a result, even if the cells CE are attached to the porous metal membrane 2, the cells CE can easily be detached from the porous metal membrane 2 (that is, the porous metal membrane can easily be backwashed) under the pressure of the fresh liquid cell culture medium CCS, and the time required to replace the liquid cell culture medium CCS can be shortened. In this case, the tubular member 4 is preferably provided with valves V1 and V2 as illustrated in FIG. 10 to prevent the liquid cell culture medium CCS collected from the container 5 from being mixed with the fresh liquid cell culture medium CCS.

In the foregoing description, the container 5 has a bottle shape. The present invention is not limited to this shape. By way of example, and not limitation, the container 5 may be a container like a beaker or may be a resin container like an intravenous drip bag. The container 5 is any container that can contain a liquid cell culture medium.

In FIG. 9 and FIG. 10, the liquid culture medium collection container 62 and the liquid culture medium storage container 72 are beakers. The present invention is not limited to beakers. Like the container 5, the liquid culture medium collection container 62 and the liquid culture medium storage container 72 may have a bottle shape and have a cap that closes the opening. According to this structure, the liquid cell culture medium CCS can be collected and replaced while the containers are sealed such that the cells CE and the liquid cell culture medium CCS are out of contact with outside air. As a result, the possibility of contamination of the cells CE and the liquid cell culture medium CCS can be reduced.

The liquid cell culture medium collecting kit for use in the liquid cell culture medium collecting method according to the preferred embodiment includes the liquid cell culture medium collecting filter unit 1. The liquid cell culture medium collecting kit may further include the container 5.

Next, the results of experiments that were carried out to study the time required to replace the liquid cell culture medium CCS in the container 5 and the proportion of cells CE remaining in the container 5 will be described. FIG. 11 is a table showing the results of those experiments. More particularly, it shows, inter alia, the proportion of cells CE remaining in the container 5 after the culture medium CCS has been sucked out of the container 5 and placed in the container 62 and the replacement time when the liquid cell culture medium in the container 5 is replaced using the liquid cell culture medium collecting filter unit 1 according to the preferred embodiment. FIG. 11 also shows the proportion of remaining cells CE and the replacement time when the liquid cell culture medium CCS in the container is replaced by using a centrifuge in a Comparative Example.

In this experiment, ras gene-introduced NIN3T3 cells were cultured by using a cell culture multiwell plate (available from Sumitomo Bakelite Co., Ltd.) with 96 wells and a U-shaped well bottom to produce 270 or more spheroids. The culture time was controlled so as to produce spheroids having a diameter of about 600 μm. The spheroids thus produced as the cells CE were added to the liquid cell culture medium CCS. The liquid cell culture medium CCS was a Dulbecco's modified Eagle's medium DMEM (High Glucose, Nacalai tesque, Inc.: 08458-45) containing 1% a penicillin-streptomycin mixed solution and 5% fetal bovine serum. A plurality of containers 5 that each contained 200 mL of a liquid cell culture medium CCS containing 30 spheroids were prepared, and a plurality of containers 5 that each contained 200 mL of a liquid cell culture medium CCS containing 60 spheroids were prepared.

Figure 7:
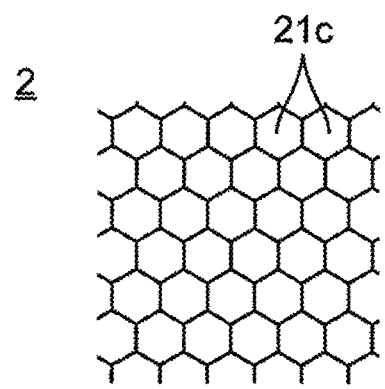
FIG. 7 is a partially enlarged plane view illustrating the schematic structure of a modification of the porous metal membrane.

As the porous metal membrane 2, a porous metal membrane having the structure illustrated in FIG. 7 (hole size (distance between opposing sides of hexagon): 100 μm, line width: 13 μm, opening ratio: 78%, honeycomb structure) and a porous metal membrane having the structure illustrated in FIG. 6 (hole size (length of sides of square): 200 μm, line width: 75 μm, opening ratio: 53%, square lattice) were used. Through the porous metal membrane, 190 mL of the liquid cell culture medium CCS (200 mL) containing either 30 or 60 spheroids was sucked from the container 5 (see FIG. 9) and deposited in container 62. At this time, the output of the pump P1 was 100 mL/min. A fresh liquid cell culture medium CCS was the supplied to the container 5 from the liquid culture medium storage container 72 until the total amount of the liquid cell culture medium CCS in the container 5 reached 200 mL. The liquid cell culture medium CCS in the container 5 was then filtered through the porous metal membrane (hole size: 50 μm), and the cells CE remaining on the porous metal membrane were observed under a microscope. The results are shown in FIG. 11.

As illustrated in FIG. 11, replacement of the liquid cell culture medium CCS containing 30 spheroids using a liquid cell culture medium collecting filter 1 unit having the porous metal membrane 2 (hole size: 100 μm) was performed twice, and the proportion of the cells CE remaining in the container 5 after each replacement operation was 86.7% and 63.3%, respectively. The two replacement operations (the operation of moving the liquid cell culture medium CCS from the culture medium storage container 72 to the container 5) was 2 minutes and 46 seconds, and 2 minutes and 35 seconds, respectively. In separate experiments, the replacement operations were performed by replacing the liquid cell culture medium CCS containing 60 spheroids using a liquid cell culture medium collecting filter unit having the porous metal membrane (hole size: 100 µm) was performed twice, and the proportion of the cells CE remaining in the container 5 after the replacement operation was 90.0% and 88.3%, respectively. The replacement work time was 2 minutes and 52 seconds, and 2 minutes and 41 seconds.

In a similar manner, the replacement of the liquid cell culture medium CCS containing 30 spheroids using a liquid cell culture medium collecting filter unit having the porous metal membrane (hole size: 200 µm) was performed twice. The proportion of the cells CE remaining in the container 5 after the two replacement operations was 90% and 96.7%, respectively. The time it took to carry out the replacement operations were 2 minutes and 45 seconds, and 2 minutes and 37 seconds, respectively. In another experiment, a liquid cell culture medium CCS containing 60 spheroids was placed in the container 5 and by using a liquid cell culture medium collecting filter unit having the porous metal membrane (hole size: 200 µm) was performed twice, and the proportion of the cells CE remaining in the container 5 was 75.0% and 96.7%. The time it took to replace the liquid cell culture medium CCS was 3 minutes and 00 seconds, and 2 minutes and 42 seconds, respectively.

In the Comparative Example, the experiment illustrated in FIG. 12A to FIG. 12F was performed by using a centrifuge.

First, a plurality of containers 5A that each contain 200 mL of a liquid cell culture medium CCS containing 30 or 60 spheroids was prepared as in the foregoing description.

Figure 12A:
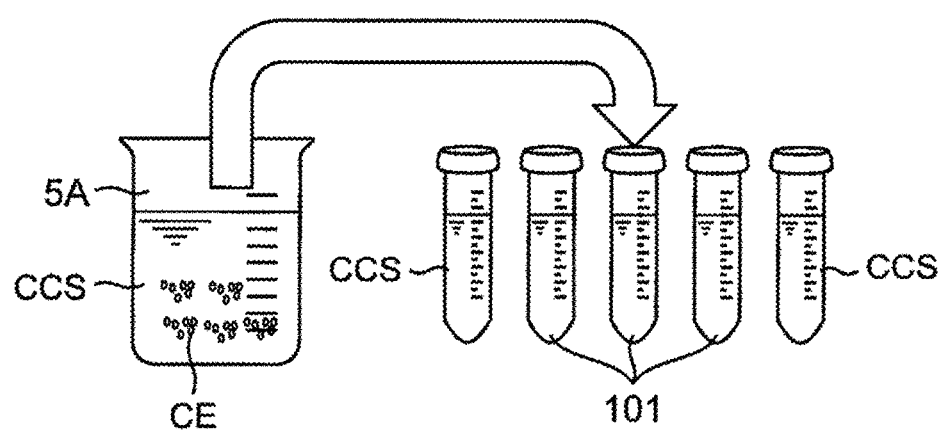
FIG. 12A is a schematic diagram illustrating the step of replacing a cell-containing liquid cell culture medium by using a centrifuge.

Next, as illustrated in FIG. 12A, 40-mL aliquots of the liquid cell culture medium CCS in the container 5A were dispensed into five centrifugation tubes 101.

Figure 12B:
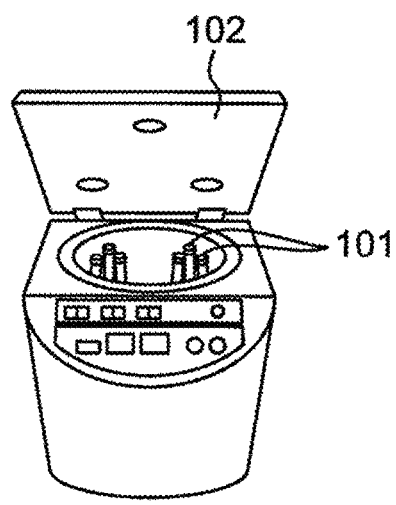
FIG. 12B is a schematic diagram illustrating the step following the step in FIG. 12A.

Next, as illustrated in FIG. 12B, the centrifugal force was applied to the centrifugation tubes 101 by using a centrifuge 102 at a rotation speed of 1000 rpm for 5 minutes.

Figure 12C:
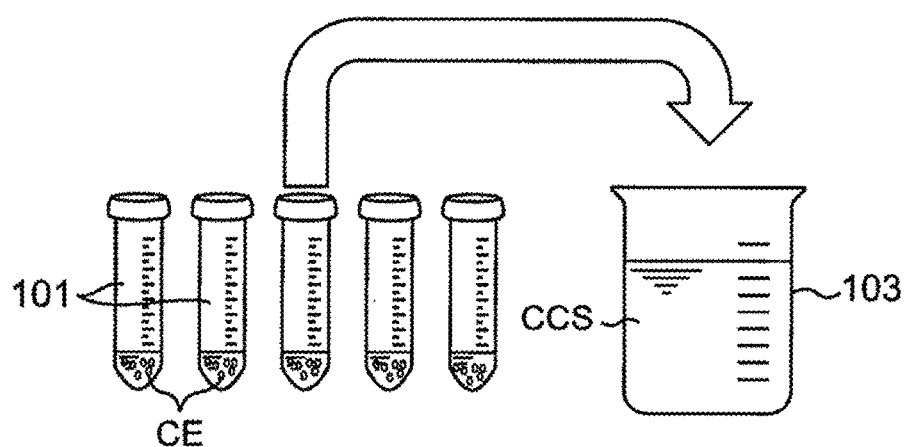
FIG. 12C is a schematic diagram illustrating the step following the step in FIG. 12B.

Next, as illustrated in FIG. 12C, the supernatant which is part of the liquid cell culture medium CCS in each centrifugation tube 101 was discarded into a waste container 103.

Figure 12D:
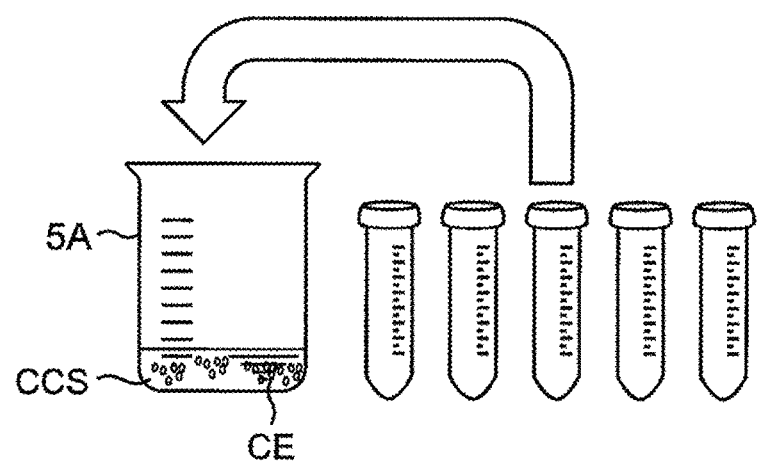
FIG. 12D is a schematic diagram illustrating the step following the step in FIG. 12C.

Next, as illustrated in FIG. 12D, the cell CE-containing liquid cell culture medium CCS that remains in each centrifugation tube 101 was returned to the container 5A.

Figure 12E:
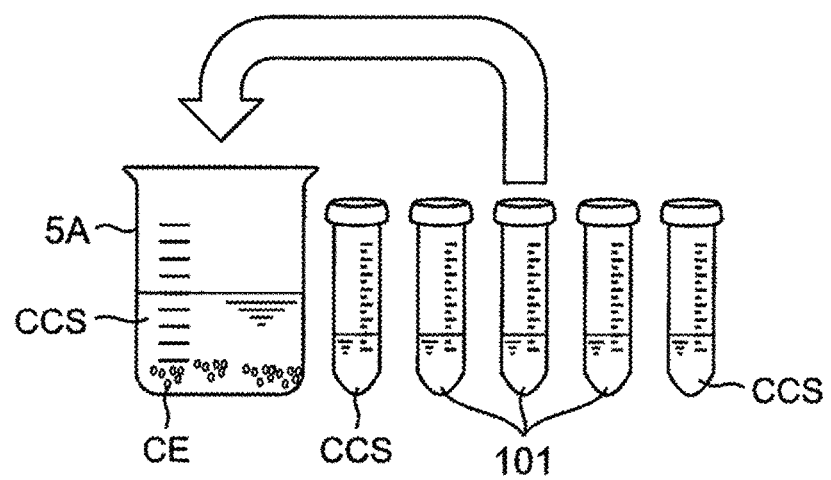
FIG. 12E is a schematic diagram illustrating the step following the step in FIG. 12D.

Next, as illustrated in FIG. 12E, 10 mL of a fresh liquid cell culture medium CCS was placed in each centrifugation tube 101, and the inside of each centrifugation tube 101 was washed with the fresh liquid cell culture medium CCS. The liquid cell culture medium CCS obtained after washing was placed in the container 5A.

Figure 12F:
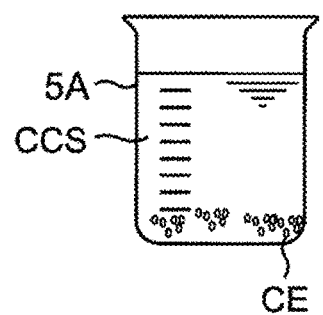
FIG. 12F is a schematic diagram illustrating the step following the step in FIG. 12E.

Next, as illustrated in FIG. 12F, the fresh liquid cell culture medium CCS was placed in the container 5A such that the total amount of the liquid cell culture medium CCS in the container 5A reached 200 mL. The liquid cell culture medium CCS in the container 5A was filtered through the porous metal membrane (hole size: 50 µm), and the cells CE remaining on the porous metal membrane were observed under a microscope. The results are shown in FIG. 11.

As illustrated in FIG. 11, the work of replacing the liquid cell culture medium CCS containing 30 spheroids by using the centrifuge 102 was performed twice, and the proportion of the cells CE remaining in the container 5A was 53.3% and 30.0%. The replacement work time was 22 minutes and 12 seconds, and 17 minutes and 53 seconds. The work of replacing the liquid cell culture medium CCS containing 60 spheroids by using the centrifuge 102 was performed twice, and the proportion of the cells CE remaining in the container 5A was 90.0% and 96.3%. The replacement work time was 21 minutes and 44 seconds, and 17 minutes and 14 seconds.

The experimental results indicate that the liquid cell culture medium collecting filter unit 1 according to the preferred embodiment can reduce variations in the proportion of the remaining cells CE (63.5% to 96.7%→30.0% to 96.3%). The experimental results also indicate that the liquid cell culture medium collecting filter unit 1 according to the preferred embodiment can greatly shorten the time required to collect the liquid cell culture medium CCS.

In the field of cell culture, a liquid culture medium containing secretes from cells may be used. The liquid culture medium is prepared by repeating the process of immersing cells in a liquid culture medium for a certain period of time, then collecting only the cells, and immersing the collected cells again for a certain period of time. In preparing the liquid culture medium, a large amount of the liquid culture medium can be prepared by using the liquid cell culture medium collecting filter unit (hereinafter abbreviated as the filter unit) 1 according to the preferred embodiment.

The results of the experiment in which a liquid culture medium is prepared by using the filter unit 1 according to the preferred embodiment will be described below.

First, a conditioned medium was prepared by adding 1 liter of a serum-free medium containing 105 CHO-RD cells/mL to a 1-liter culture container. The filter unit 1 according to the preferred embodiment was placed in the culture container. The tubular member 4 was a silicone hose (6 mm in inner diameter). The porous metal membrane 2 was a porous metal membrane (diameter of exposed portion: 6 mm, thickness: 1.2 µm, hole size (length of sides of square): 2.6 µm, line diameter: 1.0 µm, opening ratio: 52%, square lattice) made of nickel and having the structure illustrated in FIG. 6. A tubing pump was connected to the tubular member 4 at about the midpoint of the tubular member 4. One end portion of the tubular member 4 located outside the culture container was placed in a 1-liter closed collection container. In this state, the conditioned medium was left to stand for two days to culture the cells in the culture container.

The tubing pump was then operated to transfer 0.9 liters of the conditioned medium from the culture container to the collection container. The operating time of the tubing pump at this time was 30 minutes.

The filter unit 1 was then taken out of the culture container, and 100 mL of the liquid remaining in the culture container was taken out. The number of the cells in the liquid was determined with a cell counter.

As a result, the cell concentration in the liquid was 107 cells/mL. The surface of the filter unit 1 taken out of the culture container was observed under a microscope and a small number of the cells were present on the surface.

The results of the experiment in which a liquid culture medium is prepared using the filter unit according to Comparative Example will be described below.

The filter unit according to the Comparative Example was different from the filter unit 1 according to the preferred embodiment in that a porous resin membrane (hole size (diameter of circular hole): 3.0 µm, opening ratio: 20%, random arrangement) was used instead of the porous metal membrane 2. Otherwise, the filter unit according to the Comparative Example had the same structure as the filter unit 1 according to the preferred.

First, the filter unit according to the Comparative Example was placed in a culture container containing the conditioned medium, and one end portion of the tubular member located outside the culture container was placed in a 1-liter closed collection container. In this state, the conditioned medium was left to stand for two days to culture the cells in the culture container.

The tubing pump was then operated to transfer 0.9 liters of the conditioned medium from the culture container to the collection container. The operating time of the tubing pump at this time was 120 minutes.

The filter unit according to the Comparative Example was then taken out of the culture container, and 100 mL of the liquid remaining in the culture container was taken out. The number of the cells in the liquid was determined with a cell counter.

As a result, the cell concentration in the liquid was $5 \times 10^4$ cells/mL. As the surface of the filter unit according to the Comparative Example taken out of the culture container was observed under a microscope, a large number of the cells were present on the surface.

The above-described experimental results indicate that the cell concentration of the liquid remaining in the culture container in the case of using the filter unit 1 according to the preferred embodiment is 200 times higher than that in the case of using the filter unit according to the Comparative Example. In other words, the use of the filter unit 1 according to the preferred embodiment enables continuous preparation of the liquid culture medium and enables preparation of a larger amount of the liquid culture medium. Accordingly, the filter unit 1 is particularly effective when rare cells are used to prepare liquid culture media.

One of the reasons why the cell concentration of the liquid remaining in the culture container in the case of using the filter unit 1 according to the preferred embodiment is higher than that in the case of using the filter unit according to the Comparative Example may be because the porous metal membrane always contacts a large amount of the liquid cell culture medium, and the cells attached to the porous metal membrane are washed away, which makes it difficult to cause clogging. Another reason may be because the pressure required to transfer the liquid culture medium in the case of using the filter unit 1 according to the preferred embodiment is lower than that in the case of using the filter unit according to the Comparative Example, which reduces clogging caused by the cells. In particular, when the porous membrane is disposed in the hollow part of the tubular member, the pressure loss caused by the tubular member as well as the pressure loss caused by the porous membrane occur. In the filter unit according to the Comparative Example including the porous resin membrane, the pressure in the tubular member may become extremely high at the time of occurrence of clogging, and the clogging caused by the cells may become more severe. Thus, the filter unit in Example can shorten the work time and can reduce the stress on the cells. When a porous metal membrane is used as in the filter unit 1 according to the preferred embodiment, the cells attached to the porous metal membrane may easily be released into the liquid at the time of stopping of suction of the liquid culture medium, and the reduction in the number of cells in the culture container may be reduced.

Although the present invention is fully described in connection with preferred embodiments and with reference to the accompanying drawings, various modifications and alterations will be apparent to those skilled in the art. It should be understood that these modifications and alterations are within the scope of the present invention defined by the accompanying claims unless the modifications and alterations are out of the scope of the present invention.

Since the liquid cell culture medium collecting filter unit according to the present invention can reduce variations in the proportion of remaining cells and can shorten the time required to collect a liquid cell culture medium, the liquid cell culture medium collecting filter unit according to the present invention is useful to collect and replace the liquid cell culture medium.

REFERENCE SIGNS LIST

1 Liquid cell culture medium collecting filter unit
2 Porous metal membrane
2A Peripheral portion
2a First bent portion
2b Second bent portion
2c Stripe-shaped protrusion
3 Holding member
3a, 3b Main surface
4 Tubular member
4a Fitting portion
4b Hollow part
5, 5A Container
21a, 21b Main surface
21c Through-hole
31 First Frame Member
31a Flat portion
31b Through-hole
31c Protrusion
31d Flange
31e Slope surface
31f End portion
31g Through-hole
32 Second frame member
32a Flat portion
32b Through-hole
32c Protrusion
32d Protrusion
32e Slope surface
32f End portion
32g Through-hole
51 Cap
61 Collection pipe
62 Liquid culture medium collection container
71 Supply pipe
72 Liquid culture medium storage container
73 Suction pipe
101 Centrifugation tube
102 Centrifuge
103 Waste container
P1, P2 Pump

The invention claimed is:

1. A filter unit for filtering cells contained in a liquid cell culture medium, the filter unit comprising:
  a tubular member defining a liquid cell culture medium flow path having a central axis;
  a porous metal membrane comprising a central portion located in the flow path and a peripheral portion located outside of the flow path; and
  a support holding the peripheral portion of the membrane in such a manner that the central portion of the membrane is in tension and lies in a plane which is perpendicular to the central axis, the support having first and second opposed surfaces that extend at an oblique angle with respect to the central axis and hold the peripheral portion of the membrane such that the peripheral portion of the porous metal membrane is sandwiched between the first and second opposed surfaces.

2. The filter unit according to claim 1, wherein a portion of the peripheral portion that is sandwiched by the first and second opposed surfaces has at least one stripe-shaped protrusion located thereon.

3. The filter unit according to claim 2, wherein:
the portion of the peripheral portion that is sandwiched by the first and second opposed surfaces has a plurality of stripe-shaped protrusions located thereon; and
the stripe-shaped protrusions are oriented in random directions.

4. The filter unit according to claim 3, wherein the support has third and fourth opposed surfaces located radially inward of the first and second surfaces with respect to the central axis and which extend perpendicular to the central axis, the peripheral portion of the porous metal membrane extending between both the first and second and the third and fourth surfaces, respectively.

5. The filter unit according to claim 1, wherein the support includes a protrusion member that extends parallel to the central axis and is located radially outward of the peripheral portion of the porous metal membrane with respect to the central axis.

6. A liquid cell culture medium collecting method, comprising:
(a) placing a liquid cell culture medium collecting filter unit in a container that contains a cell-containing liquid cell culture medium, the liquid culture medium collecting filter unit including:
a tubular member defining a liquid cell culture medium flow path having a central axis;
a porous metal membrane that filters out cells in the liquid cell culture medium, the porous metal membrane having a central portion located in the flow path and a peripheral portion located outside of the flow path; and
a support holding the peripheral portion of the porous metal membrane in such a manner that the central portion of the membrane is in tension and lies in a plane which is perpendicular to the central axis, the support having first and second opposed surfaces that extend at an oblique angle with respect to the central axis and hold the peripheral portion of the membrane such that the peripheral portion of the porous metal membrane is sandwiched between the first and second opposed surfaces; and
(b) passing the liquid cell culture medium in the container through the flow path and the porous metal membrane and collecting the liquid cell culture medium outside the container.

7. The liquid cell culture medium collecting method according to claim 6, further comprising supplying a fresh liquid cell culture medium to the container after at least some of the liquid cell culture medium has been collected outside the container.

8. The liquid cell culture medium collecting method according to claim 7, wherein:
the liquid cell culture medium in the container passes through the porous metal membrane in a first direction as it is being moved from the container to a location outside the container; and
the fresh liquid cell culture medium passes through the porous metal membrane in a second direction, opposite to the first direction, as it is supplied to the container.

9. The liquid cell culture medium collecting method according to claim 8, further comprising, after the fresh liquid cell culture medium has been supplied to the container, causing at least some of the liquid cell culture medium located in the container to flow through the flow path and the porous metal membrane and collecting the liquid cell culture medium outside the container.

10. The liquid cell culture medium collecting method according to claim 7, further comprising, after the fresh liquid cell culture medium has been supplied to the container supplying, causing at least some of the liquid cell culture medium located in the container to flow through the flow path and the porous metal membrane and collecting the liquid cell culture medium outside the container.

* * * * *